US00PP27446P2

(12) United States Plant Patent
Egger

(10) Patent No.: US PP27,446 P2
(45) Date of Patent: Dec. 6, 2016

(54) ***KNIPHOFIA* PLANT NAMED 'TNKNIPR'**

(50) Latin Name: ***Kniphofia* spp.**
Varietal Denomination: TNKNIPR

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 59 days.

(21) Appl. No.: 14/545,491

(22) Filed: May 12, 2015

(51) Int. Cl.
*A01H 5/02* (2006.01)

(52) U.S. Cl.
USPC ..... Plt./443

(58) Field of Classification Search
USPC ..... Plt./443
See application file for complete search history.

(56) References Cited

PUBLICATIONS

UPOV hit on 'TNKNIPR', QZ PBR 20151920, published Dec. 15, 2015.*

* cited by examiner

*Primary Examiner* — Anne Grunberg
(74) *Attorney, Agent, or Firm* — Klarquist Sparkman, LLP

(57) ABSTRACT

A new and distinct *Kniphofia* plant characterized by its habit of forming multiple crowns fast and each crown produces inflorescences in the first season, large inflorescences of red flowers on short stems, a very long bloom time with repeat blooming from July through October in Canby, Oreg., a short habit, narrow, grassy leaves, and excellent vigor.

1 Drawing Sheet

Botanical denomination: *Kniphofia* spp.
Cultivar designation: 'TNKNIPR'.

BACKGROUND OF THE INVENTION

The present invention relates to a new and distinct *Kniphofia*, and given the cultivar name is 'TNKNIPR'. *Kniphofia* is in the family Xanthorrhoeaceae. 'TNKNIPR' is a hybrid resulting from a planned breeding program to produce short, compact, reblooming *Kniphofia*. The cross was made using the following proprietary, unreleased plants: *Kniphofia* K85-6, as the seed parent and *Kniphofia* K90-1, as the pollen parent. It was selected for best habit, flower color, reblooming, and crown count from many seedlings of the cross in Canby, Oreg.

Compared to *Kniphofia* K85-6, the seed parent, the new cultivar is more free flowering and has a shorter habit.

Compared to *Kniphofia* K90-1, the pollen parent, the new cultivar is more free flowering and has a red flowers rather than cream and red.

Compared to *Kniphofia* 'Red Hot Popsicle', U.S. Plant Pat. No. 24,036, the new cultivar is ⅓ shorter.

SUMMARY OF THE INVENTION

The new cultivar is unique and characterized by:

1. its habit of forming multiple crowns fast and each crown produces inflorescences in the first season,
2. large inflorescences of red flowers on short stems,
3. a very long bloom time with repeat blooming from July through October in Canby, Oreg.,
4. a short habit,
5. narrow, grassy leaves, and
6. excellent vigor.

This new cultivar has been reproduced only by asexual propagation (division, tissue culture). Each of the progeny exhibits identical characteristics to the new cultivar. Asexual propagation by leaf cuttings, tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows 12-month-old *Kniphofia* 'TNKNIPR' in the ground in the trial field in August in Canby, Oreg.

DETAILED PLANT DESCRIPTION

The following is a detailed description of the new *Kniphofia* cultivar based on observations of 8-month-old specimens growing outside in full sun in Canby, Oreg. These were planted as 4" plants in late May. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart,* 5$^{th}$ edition, 2007.

Plant:

*Type*.—Rhizomatous herbaceous perennial.
*Hardiness*.—USDA Zones 7 to 9.
*Size*.—Grows to 60 cm wide and 39 cm tall from the top of the soil to the top of the foliage.

*Crown #.*—About 40.
*#Leaves/crown.*—About 10.
*#Inflorescences/crown.*—1 to 2.
*Form.*—Clumping.

Leaf:
*Type.*—Simple.
*Shape.*—Strap-like, keeled.
*Arrangement.*—Basal rosette.
*Blade size.*—28 cm to 55 cm long and 6 mm to 10 mm wide.
*Margins.*—Entire.
*Apex.*—Acuminate.
*Base.*—Clasping.
*Surface texture.*—Glabrous on topside, glaucous on the bottom side.
*Venation.*—Parallel.
*Color.*—Top and bottom side Green 137A.

Inflorescence:
*Type.*—Spike-like scapose raceme.
*Number of flowers per raceme.*—About 150.
*Inflorescence.*—12 cm long and 5 cm wide.
*Peduncle description.*—Grows to 33 cm long and 8.5 mm wide, glaucous, Yellow Green 146B.
*Pedicle description.*—1.5 mm long, glabrous, Greyed Orange 165B.
*Bloom time.*—July through October in Canby, Oreg.
*Lastingness.*—An inflorescence lasts for 2 to 4 weeks depending on the temperature.

Flower bud:
*Size.*—24 mm long and 4 mm wide.
*Shape.*—Cylindrical.
*Surface texture.*—Glabrous.
*Color.*—Red 42A.

Flower:
*Type.*—Actinomorphic.
*Shape.*—Cylindrical and tubular.
*Size.*—Grows to 28 mm deep and 7 mm wide.
*Texture.*—Waxy.
*Surface texture.*—Glabrous on both sides.
*Corolla description.*—27 mm long and 7 mm wide, 6 to 8-lobed fused tepals, tube 25 mm long and 5 mm wide, lobes reflex, each 2 mm wide and 3 mm long, ovate, entire, obtuse to acute, outside Red 42B, inside Red 39B with Red 42B on the main veins.
*Pistil description.*—One, 29 mm long, ovary 2 mm long 1.5 mm wide, Yellow Green 146C, style 27 mm long, Red 38C at base darkening to 39A near stigma, stigma White NN155A.
*Stamen.*—6, 25 mm long, filaments 24 mm long, White NN155B, anthers 1 mm long and Yellow Orange 21C darkening in areas to Greyed Orange 177A, pollen none.
*Fragrance.*—None.

Fruit and seed: None.

Pest and diseases: Pests and diseases are infrequent on *Kniphofia* spp. No problems have been observed on this plant grown under commercial conditions in Canby, Oreg.

I claim:

1. A new and distinct *Kniphofia* plant as herein shown and described.

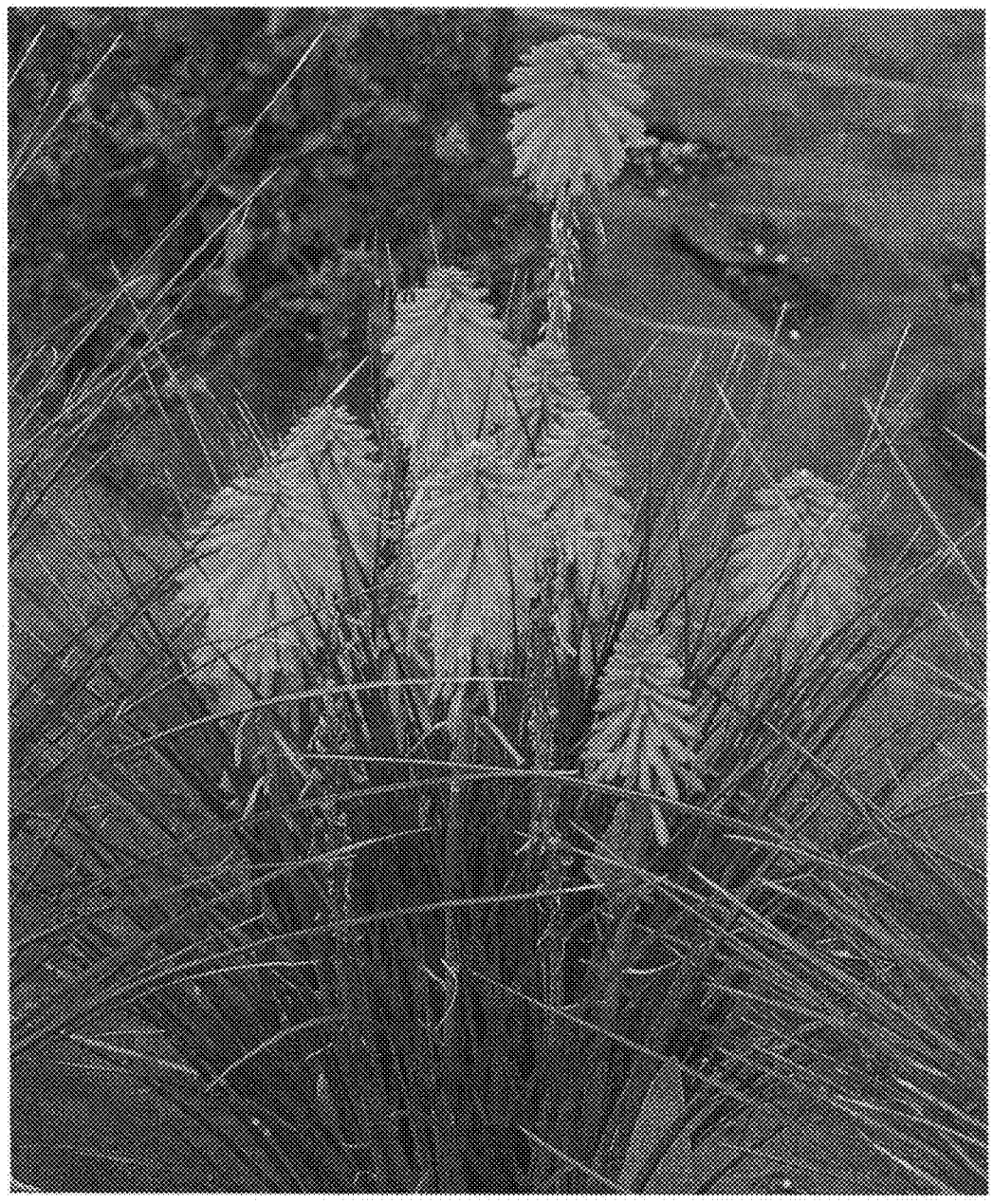

* * * * *